US012661505B2

(12) United States Patent
Hsu et al.

(10) Patent No.: US 12,661,505 B2
(45) Date of Patent: Jun. 23, 2026

(54) WEARABLE BRAIN MULTI-STIMULATION PAIN CONTROL DEVICE

(71) Applicants:METABRAIN TECHNOLOGY PTE. LTD., Singapore (SG); ZHUHAI ULOOK METABRAIN MEDICAL TECHNOLOGY CO., LTD., Zhuhai City (CN)

(72) Inventors: Chen-Chao Hsu, Taichung City (TW); Shin-Da Lee, Taichung (TW); Cheng-Ju Wu, Changhua County (TW)

(73) Assignees: METABRAIN TECHNOLOGY PTE. LTD., Singapore (SG); ZHUHAI ULOOK METABRAIN MEDICAL TECHNOLOGY CO., LTD., Zhuhai City (CN)

( * ) Notice: Subject to any disclaimer, the term of this patent is extended or adjusted under 35 U.S.C. 154(b) by 882 days.

(21) Appl. No.: 17/896,343

(22) Filed: Aug. 26, 2022

(65) Prior Publication Data

US 2023/0066923 A1     Mar. 2, 2023

(30) Foreign Application Priority Data

Aug. 27, 2021    (TW) ................................. 110131807

(51) Int. Cl.
*A61N 1/36* (2006.01)
*A61B 5/053* (2021.01)
*A61H 39/04* (2006.01)
*A61N 5/067* (2006.01)

(52) U.S. Cl.
CPC .......... *A61N 1/36021* (2013.01); *A61B 5/053* (2013.01); *A61H 39/04* (2013.01); *A61N 5/067* (2021.08)

(58) Field of Classification Search
None
See application file for complete search history.

(56) References Cited

U.S. PATENT DOCUMENTS

| 2016/0022981 | A1* | 1/2016 | Wingeier | ........... | A61N 1/36025 |
| | | | | | 607/139 |
| 2016/0136044 | A1* | 5/2016 | Liang | .................... | A61B 5/0532 |
| | | | | | 607/72 |
| 2017/0165485 | A1* | 6/2017 | Sullivan | ............... | A61B 5/0022 |
| 2017/0216577 | A1* | 8/2017 | Nguyen | ................. | A61B 5/369 |
| 2020/0069966 | A1* | 3/2020 | Porter | ................ | G02B 27/0172 |
| 2020/0382884 | A1* | 12/2020 | Chang | .................... | A61H 39/00 |

* cited by examiner

*Primary Examiner* — Mallika D Fairchild
(74) *Attorney, Agent, or Firm* — MUNCY, GEISSLER, OLDS & LOWE, P.C.

(57) ABSTRACT

A wearable brain multi-stimulation pain control device is provided, comprising a main support unit, an auxiliary support unit, an audio stimulation unit, and an optical frequency-flashed stimulation unit. The main support unit includes two ear portions corresponding to a user's ears and a front side portion, and the auxiliary support unit includes a mounting portion. Two opposite ends of the mounting portion are pivoted to the main support unit, and the audio stimulation unit includes two speakers that are respectively arranged on the ear portions and can broadcast a binaural beats with frequency following response. The optical frequency-flashed stimulation unit is arranged on the front side portion and can stimulate at least one eye of the user with flickering light, so that the user can obtain multiple stimulations at the same time in a single course of treatment to achieve the effect of improving pain.

19 Claims, 12 Drawing Sheets

WEARABLE BRAIN MULTI-STIMULATION PAIN CONTROL DEVICE

BACKGROUND OF THE INVENTION

Field of the Invention

The present invention relates to a wearable device, in particular to a wearable brain multi-stimulation pain control device.

Description of the Prior Art

In recent years, pain has always been a common disease in the field of long-term care and rehabilitation, including frozen shoulder (adhesive capsulitis), arthritis, lower back pain, etc. After the pain is recognized from the terminal nerve through the spinal cord, brain stem to the hypothalamus, and finally transmitted to the cerebral cortex to determine its response. The brain is the center of all senses, and the pain is also the responsibility of specific cortical areas of the brain. Pain is not a single feeling generated by specific stimuli, but a complex perceptual experience like vision or hearing. At present, most of the pain treatments focus on local pain relief and taking analgesic drugs, so the auxiliary devices without drugs are still to be developed.

SUMMARY OF THE INVENTION

Therefore, it is an object of the present invention to provide a wearable brain multi-stimulation pain control device that overcomes the disadvantages of the prior art.

Therefore, the wearable brain multi-stimulation pain control device of the present invention is used by a user. The wearable brain multi-stimulation pain control device includes a main support unit, an auxiliary support unit, an audio stimulation unit, an optical frequency-flashed stimulation unit, and a control unit.

The main support unit corresponds to the user's head shape, and includes two ear portions corresponding to both ears of the user, a back side portion adjacent to the ear portions and span the back of the user's skull, and a front side portion adjacent to the ear portions and span the user forward. An imaginary line passing through the main support unit and adjacent to the ears portion is defined as a reference axis, and the auxiliary support unit includes a mounting portion corresponding to the user's head shape. The two opposite ends of the mounting portion can be pivoted on the main support unit around the reference axis, and the angle can be adjusted along the outer side of the user's head. The audio stimulation unit includes two speakers respectively arranged at the ear portions, which are used to broadcast a binaural beats with frequency following response to both ears of the user, and the binaural beats with frequency following response has an audio frequency difference. The optical frequency-flashed stimulation unit is arranged at the front side portion and can stimulate at least one eye of the user with flickering light. The control unit is electrically connected with the speakers and the optical frequency-flashed stimulation unit, stores the digital information of the binaural beats with frequency following response, and can simultaneously control the speakers to broadcast the binaural beats with frequency following response according to a preset command, and the optical frequency-flashed stimulation unit displays a flickering light.

The efficacy of the present invention lies in: by arranging the speakers and the optical frequency-flashed stimulation unit, the user can simultaneously obtain multiple stimulation in a single course of treatment, thus achieving the effect of improving pain.

BRIEF DESCRIPTION OF THE DRAWINGS

Other features and effects of the present invention will appear clearly in the embodiments with reference to the drawings, wherein.

DETAILED DESCRIPTION OF THE PREFERRED EMBODIMENTS

Figure 1:
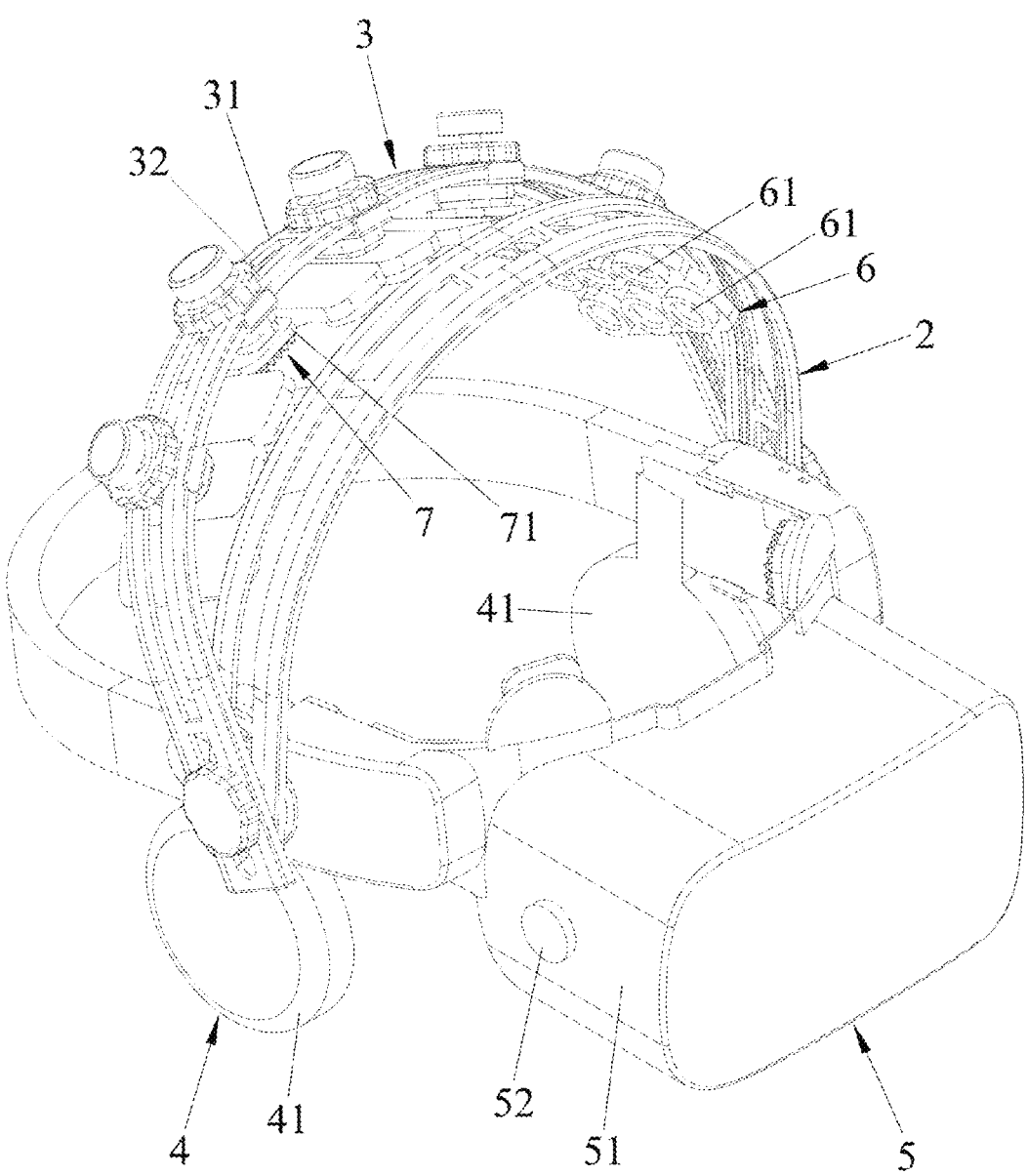
FIG. 1 is a perspective view of an embodiment of the wearable brain multi-stimulation pain control device of the present invention.
Figure 2:
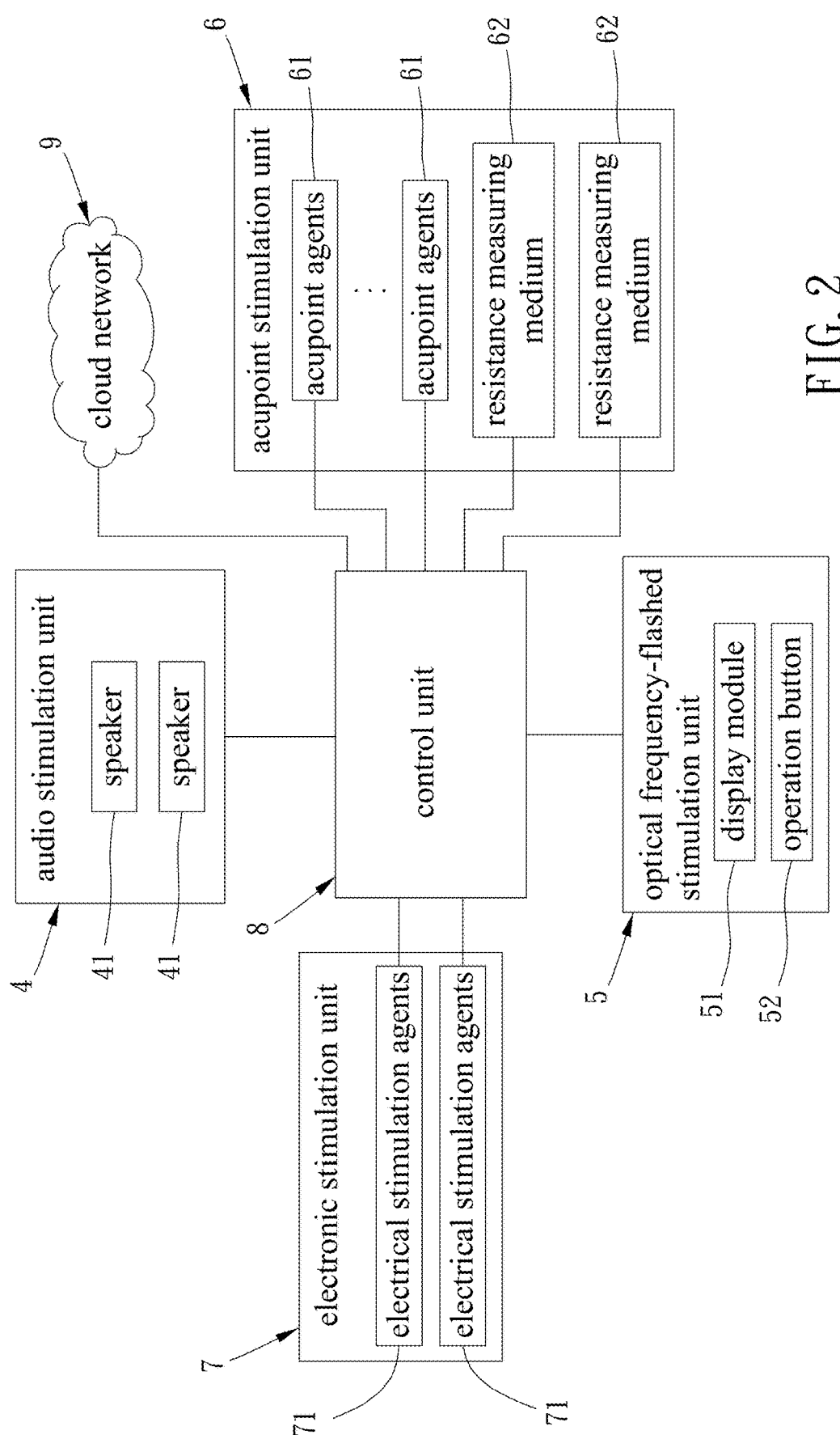
FIG. 2 is a system block diagram of the embodiment and a cloud network.

Referring to FIGS. 1 and 2, an embodiment of the wearable brain multi-stimulation pain control device of the present invention is used for a user, and the wearable brain multi-stimulation pain control device includes a main support unit 2, an auxiliary support unit 3, an audio stimulation unit 4, an optical frequency-flashed stimulation unit 5, an acupoint stimulation unit 6, an electronic stimulation unit 7, and a control unit 8.

Figure 3:
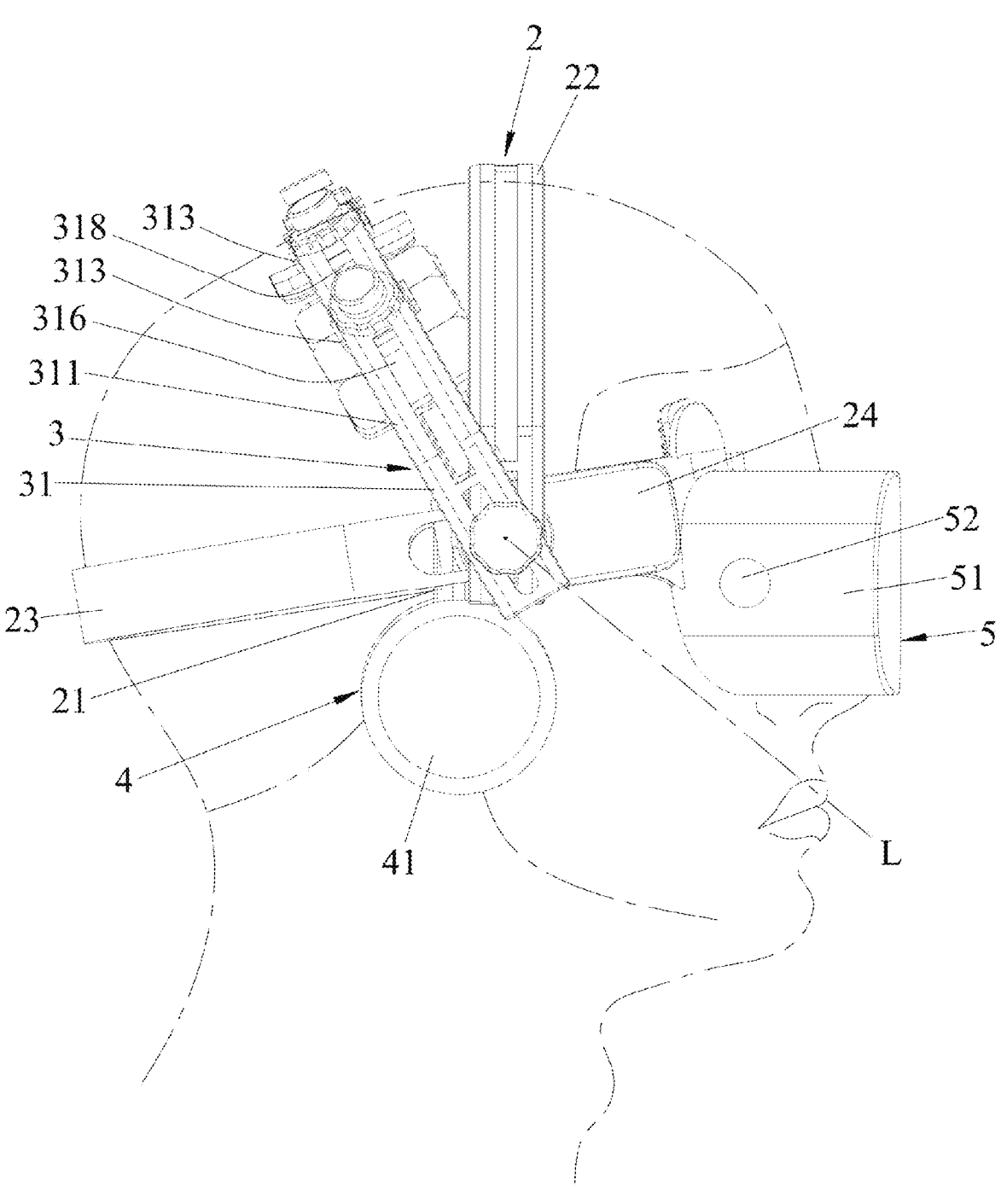
FIG. 3 is a side view of this embodiment.
Figure 4:
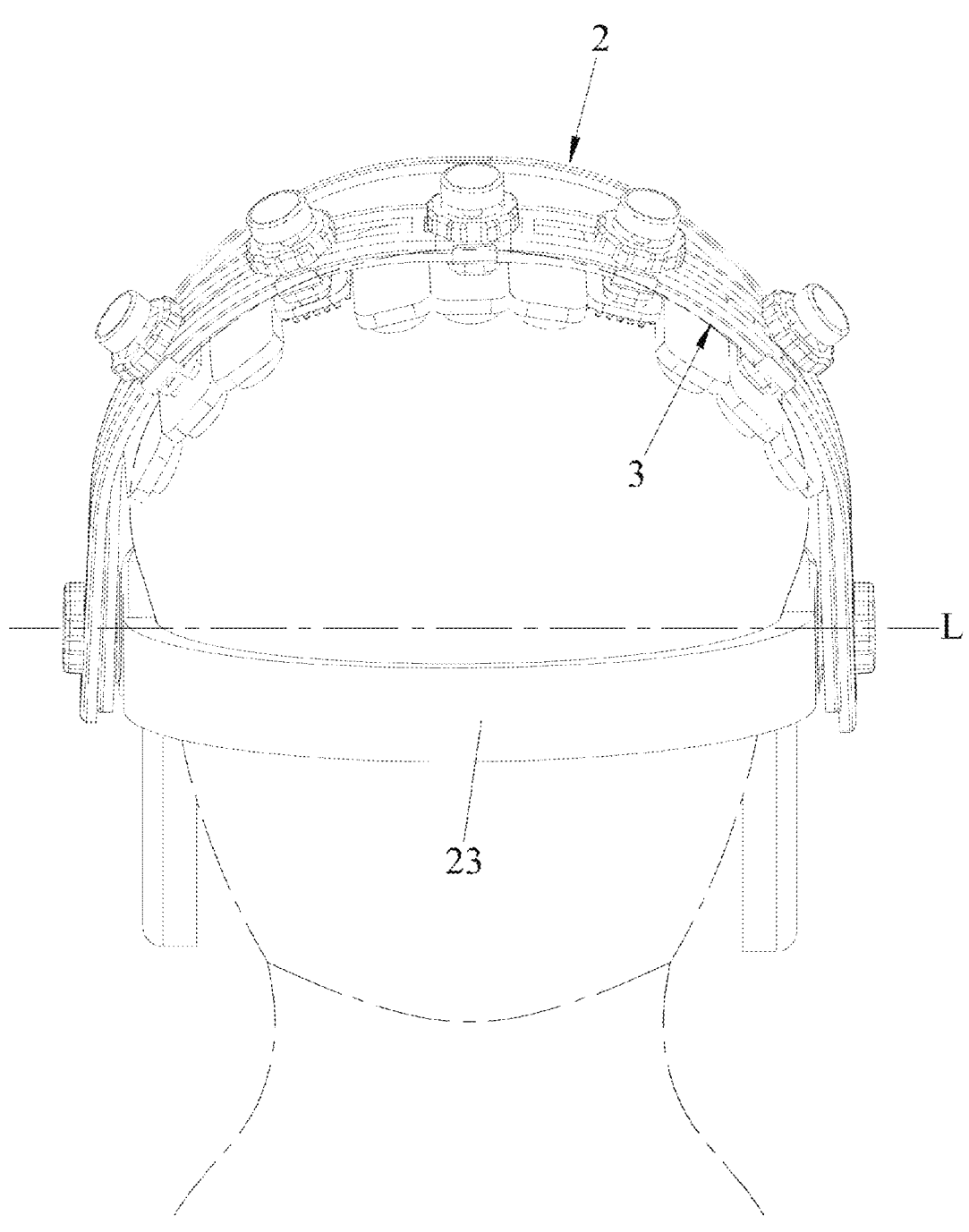
FIG. 4 is a rear view of this embodiment.
Figure 5:
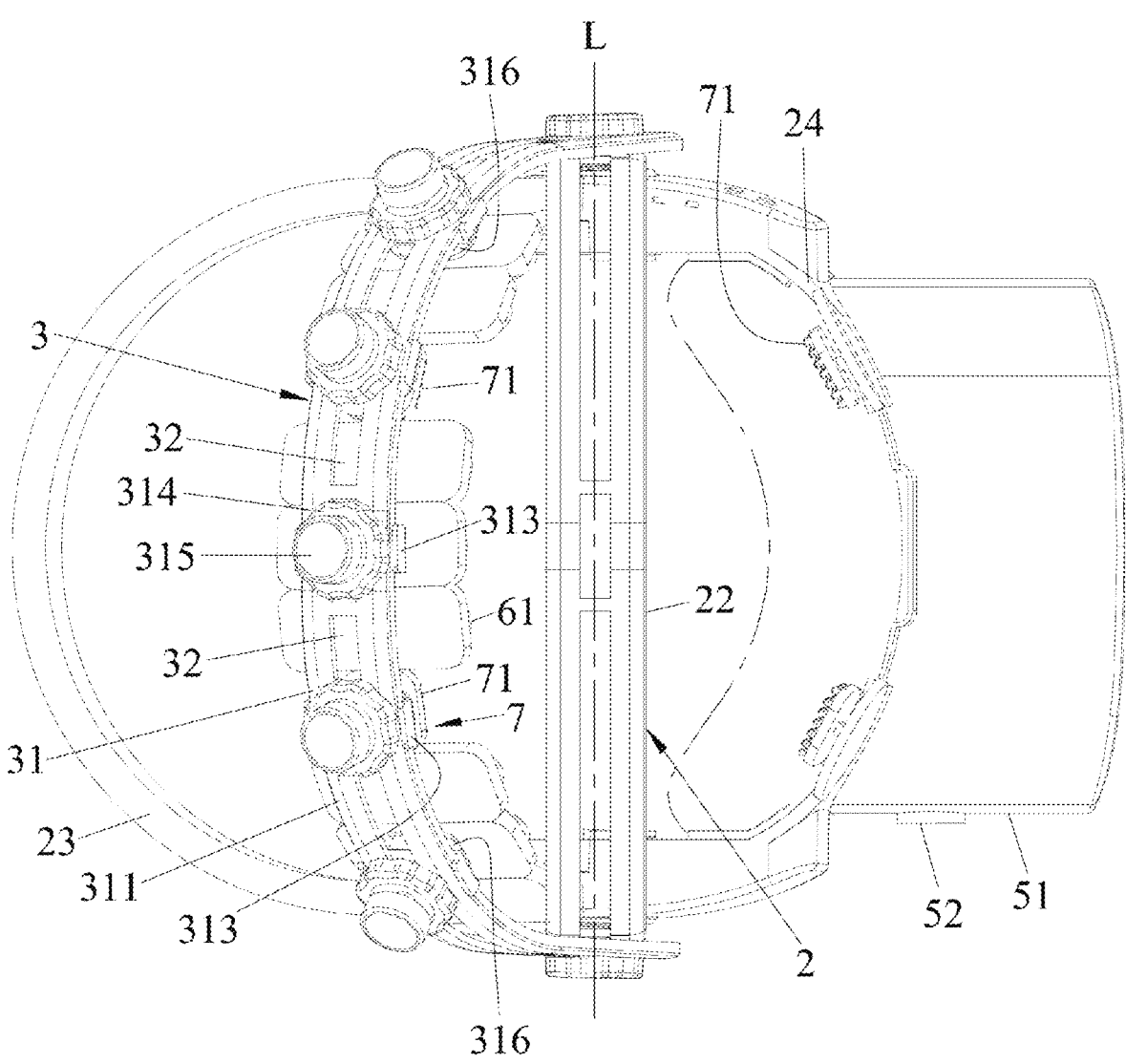
FIG. 5 is a plan view of this embodiment.

Referring to FIGS. 3, 4, and 5, the main support unit 2 corresponds to the user's head shape, and includes two ears portion 21 corresponding to both ears of the user, a top side portion 22 connected between the ears portions 21 and spans the up side of the user's skull, a back side portion 23 that is connected to the top side portion 22 adjacent to the ear portions 21 and spans the back of the user's skull, and a front side portion 24 connected to the top side portion 22 adjacent to the ear portions 21 and spanning the user forward.

The auxiliary support unit 3 includes a mounting portion 31 corresponding to the user's head shape, and a mounting slots 32 located on the mounting portion 31 at three-phase intervals and extending between the ear portions 21.

An imaginary line passing through the top side portion 22 adjacent to the ears portion 21 is defined as a reference axis L. The two opposite ends of the mounting portion 31 are rotatably pivoted on the top side portion 22 around the reference axis L, and the angle can be adjusted along the outside of the user's head.

Figure 6:
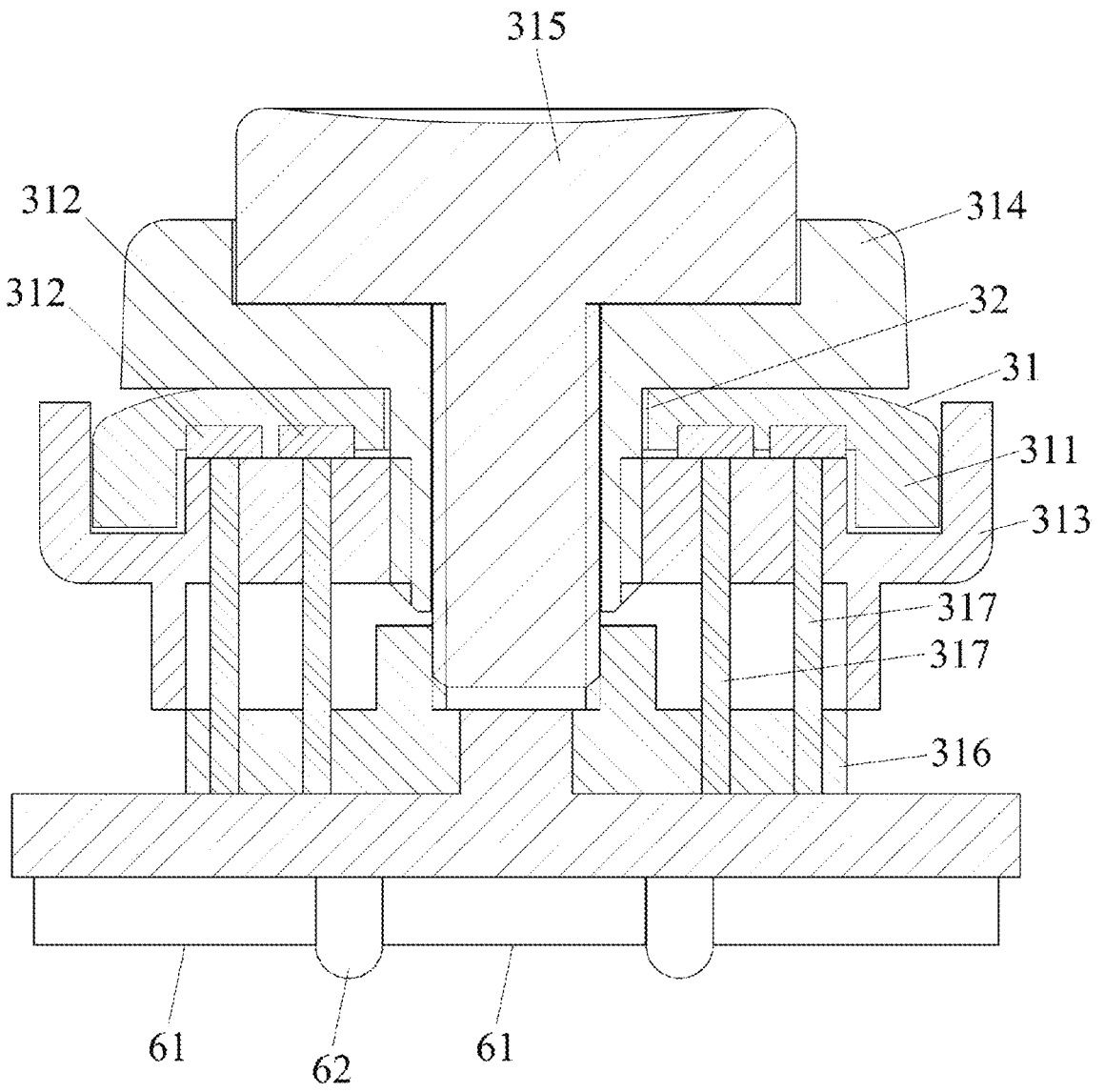
FIG. 6 is a schematic cross-sectional view illustrating the arrangement relationship between a mounting base and an acupoint agents.
Figure 7:
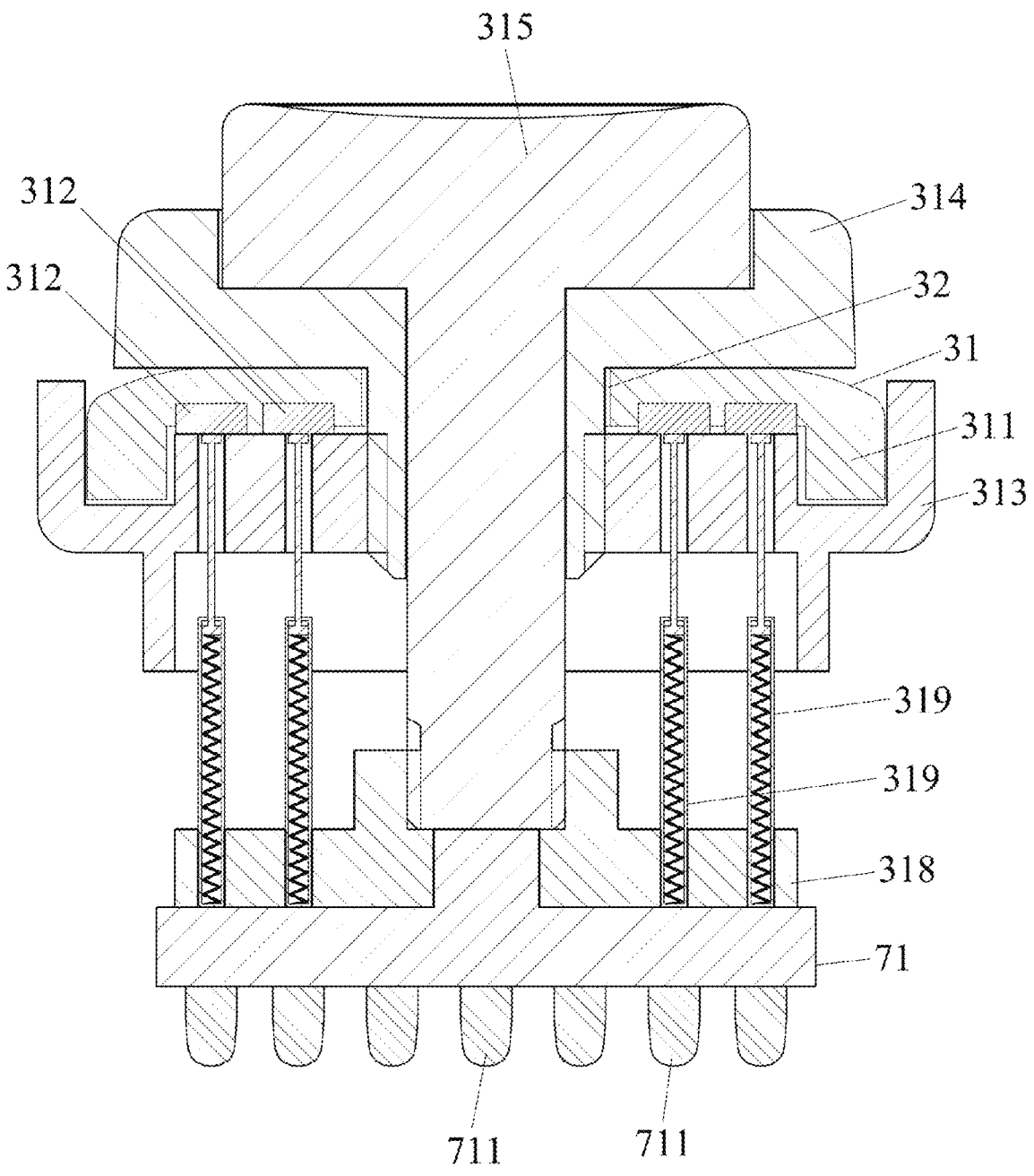
FIG. 7 is a schematic cross-sectional view illustrating the installation relationship between the mounting base and an electrical stimulation agents, and illustrating the state of the four elastic conductive members when they are not compressed.

Referring to FIGS. 5, 6 and 7, the mounting portion 31 has a rail member 311 corresponding to the user's head shape, four conductive strips 312 arranged at intervals on one side of the rail portion 311 corresponding to the user and extending between the ears portions 21, five sliding members 313 arranged on one side of the conductive strips 312 corresponding to the user and capable of changing positions along the rail member 311, five screw locking members 314 that pass through the corresponding mounting slots 32 from one side of the rail member 311, which are opposite to the sliding members 313, and are respectively screwed to the sliding members 313 for fixing the sliding members 313, five positioning members 315 respectively slidably passed through the screw locking members 314 from one side of the screw locking members 314, which are opposite to the sliding members 313, three laser mounting bases 316 that are arranged on one side of the sliding members 313, which are opposite to the rail member 311, and respectively screwed to three of the positioning members 315, several conductive members 317, two electrode mounting bases 318 that are arranged on one side of the sliding members 313, which are opposite to the rail member 311, and respectively screwed to two of the positioning members 315, and several compressible elastic conductive members 319.

Figure 8:
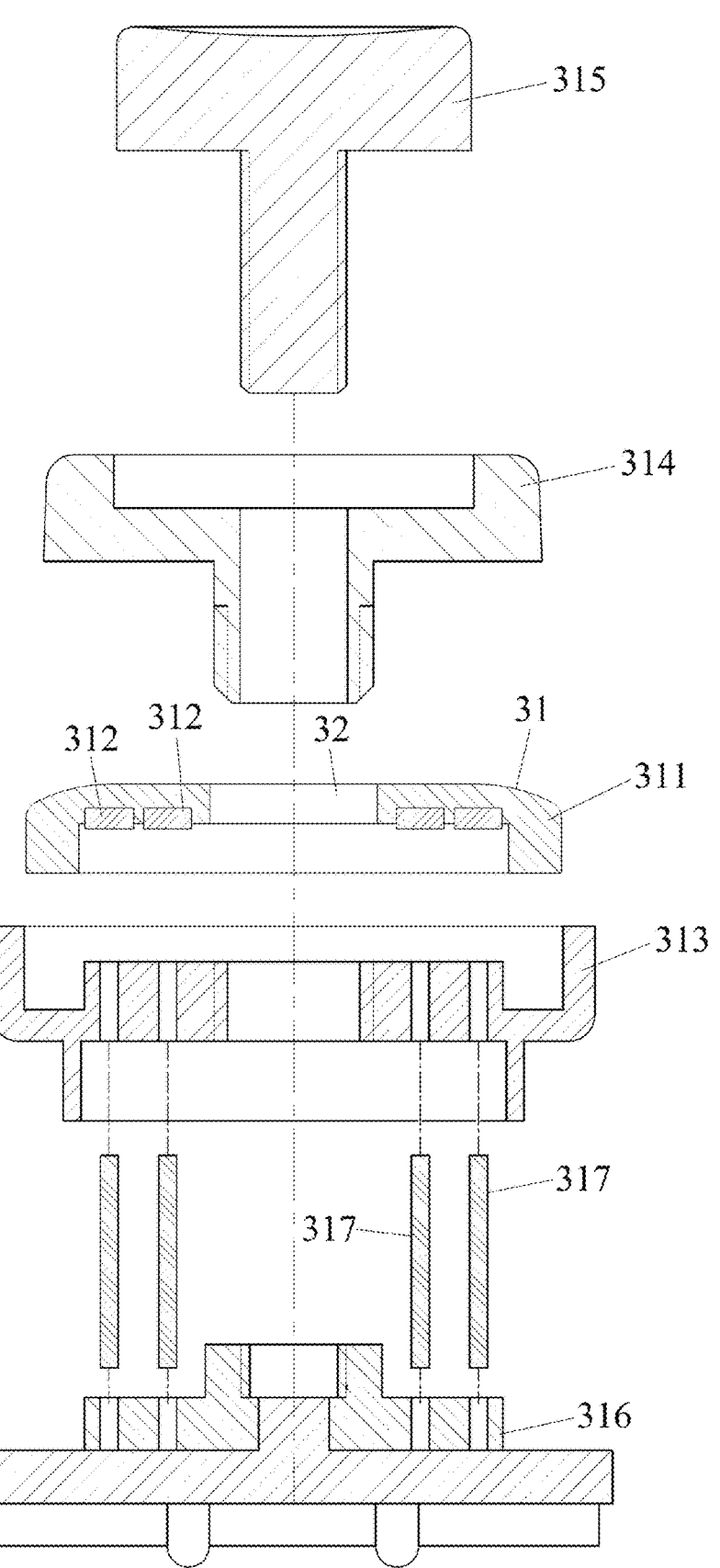
FIG. 8 is an exploded view of FIG. 6.

Referring to FIGS. 6 and 8, the number of connecting conductive members 317 corresponding to each laser mounting base 316 is the same as that of the conductive strips 312, and the connecting conductive members 317 corresponding to each laser mounting base 316 pass through the corresponding sliding member 313 and the laser mounting base 316, and one end is electrically connected to the corresponding conductive strips 312.

Figure 9:
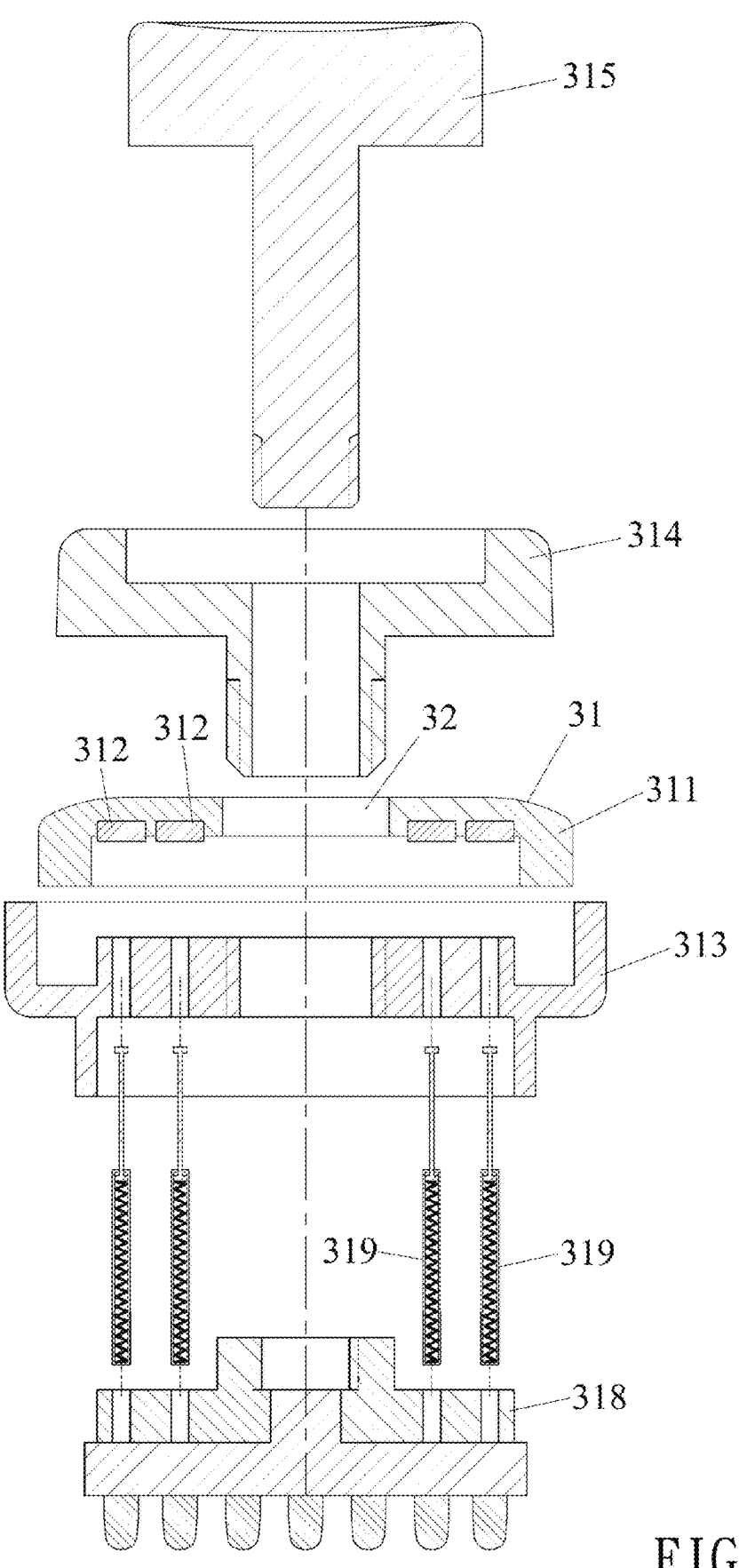
FIG. 9 is an exploded view of FIG. 7.
Figure 10:
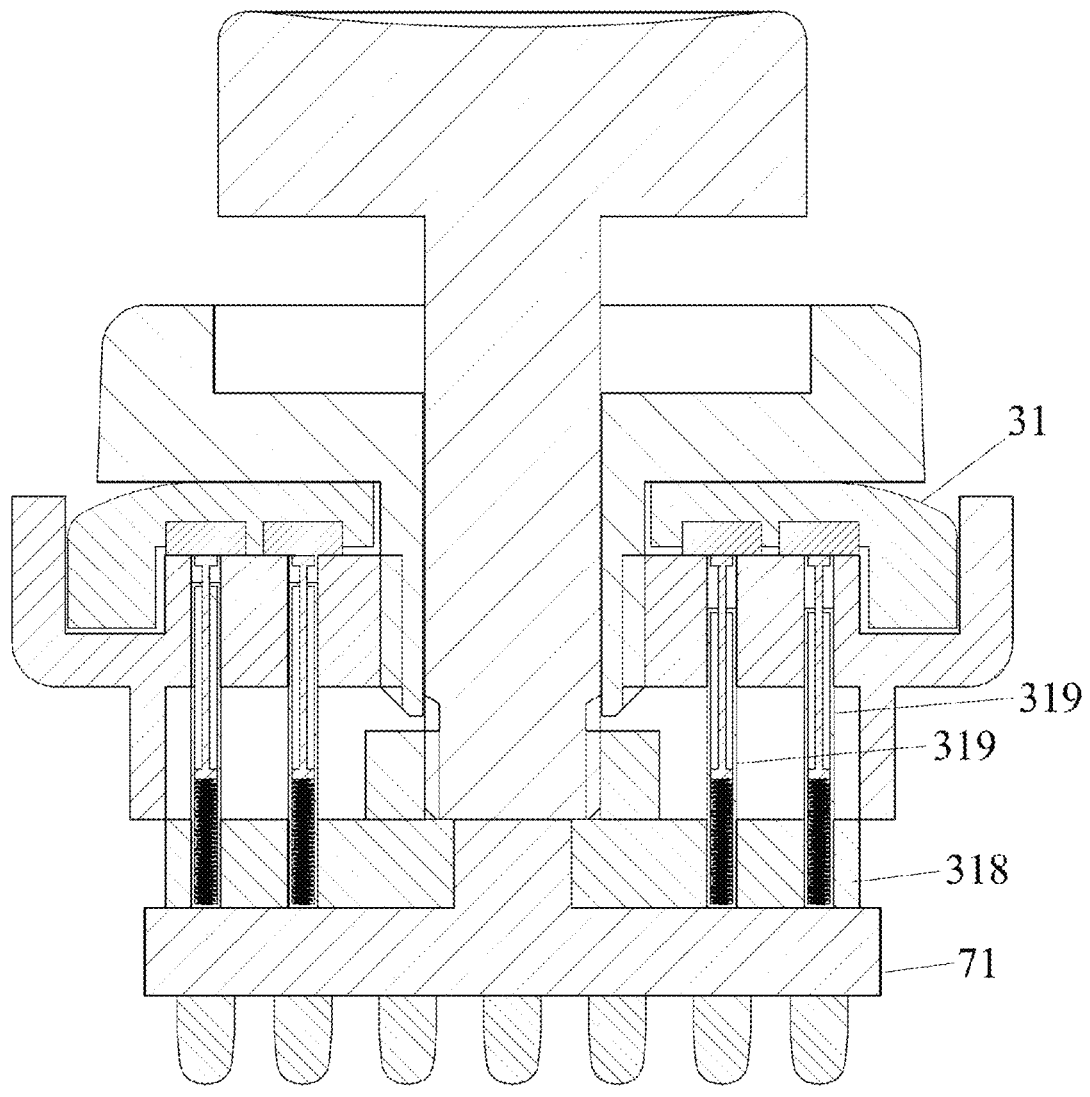
FIG. 10 is a view similar to FIG. 7, illustrating the state when the elastic conductive members are compressed.

Referring to FIGS. 7, 9 and 10, the number of elastic conductive members 319 corresponding to each electrode mounting base 318 is the same as the number of conductive strips 312, and the elastic conductive members 319 corresponding to each electrode mounting base 318 pass through the corresponding sliding member 313 and the electrode mounting base 318, and one end is electrically connected to the corresponding conductive strips 312.

Referring to FIGS. 1, 2 and 3, the audio stimulation unit 4 includes two speakers 41 respectively arranged at the ears portions 21, and the speakers 41 are used to broadcast a binaural beats with frequency following response to both ears of the user, and the binaural beats with frequency following response has an audio frequency difference. In this embodiment, the audio frequency difference of the binaural beats with frequency following response is between 1 Hz to 20 Hz.

The optical frequency-flashed stimulation unit 5 is arranged on the front side portion 24 and can stimulate the eyes of the user with flickering light. In this embodiment, the light frequency stimulation unit 5 is a virtual image wearable display, and the optical frequency-flashed stimulation unit 5 corresponds to both eyes of the user, but in other embodiments, the optical frequency-flashed stimulation unit 5 may also correspond to one of the eyes of the user. The light frequency stimulation unit 5 includes a display module 51 and an operation button 52.

Figure 11:
FIG. 11 is a display schematic diagram of a display module of this embodiment.

The flickering light displayed by the optical frequency-flashed stimulation unit 5 can flicker at a predetermined frequency or stimulate the user's eyes with a difference in optical frequency. In this embodiment, the flickering light displayed by the optical frequency-flashed stimulation unit 5 through the display module 51 flickering at the predetermined frequency ranging from 1 Hz to 20 Hz, and the generated light is green light with a wavelength ranging from 495 nm to 570 nm, so that the rectangular flickering light 511 (see FIG. 11) appears at the outer frame of the virtual image, but the form is not limited to this. When the user's eyes are stimulated respectively by the optical frequency difference, the flickering light displayed by the optical frequency-flashed stimulation unit 5 stimulates the user's eyes respectively with the optical frequency difference, and the generated light is green light with a wavelength between 495 nm and 570 nm, and the optical frequency difference is between 1 Hz to 20 Hz.

Referring to FIGS. 1, 2, and 6, the acupoint stimulation unit 6 includes several acupoint agents 61 installed on the laser mounting base 316 of the mounting portion 31 in adjustable positions, and three groups of resistance measuring medium 62 adjacent to the acupoint agents 61, each of which is used to measure the user's body resistance to confirm whether the corresponding acupoint agents 61 is located in a low-resistance acupoint area. The acupoint agents 61 are electrically connected to one end of the corresponding connecting conductive members 317 opposite to the conductive strips 312. The acupoint agents 61 can move along the mounting slot 32 with the laser mounting base 316 to adjust their positions. The acupoint agents 61 are used to output the physical stimulation of laser light to the user's head acupoints. In this embodiment, the laser light wavelength of the acupoint agents 61 is between 500 nm and 1300 nm, and the output power is between 5 MW and 500 MW. Each laser mounting base 316 is used for mounting nine acupoint agents 61, but it is not limited to this.

The positions of the acupoint agents 61 are between the anterior oblique line of vertex-temporal and posterior oblique line of vertex-temporal of the user, and at least one of the acupoint agents 61 can be adjusted to the middle line of vertex (between Baihui acupoint GV20 and the Qianding acupoint GV21, international scalp acupuncture lines code MS5) corresponding to the user when the angle of the auxiliary support unit 3 is adjusted, One of the acupoint agents 61 can be adjusted to the anterior oblique line of vertex-temporal (between Qianding acupoint GV21 and Xuanli acupoint GB6, international scalp acupuncture lines code MS6) corresponding to the user when the angle of the mounting portion 31 is adjusted, and One of the acupoint agents can be adjusted to the posterior oblique line of vertex-temporal (between Baihui acupoint GV20 and Qubin acupoint GB7, international scalp acupuncture lines code MS7) corresponding to the user when the angle of the mounting portion 31 is adjusted, One of the acupoint agents 61 can be adjusted to the lateral line 1 of vertex (from Chengguang acupoint BL6 backward along the meridian, international scalp acupuncture lines code MS8) corresponding to the user when the angle of the mounting portion 31 is adjusted, and One of the acupoint agents 61 can be adjusted to the lateral line 2 of vertex (from Zhengying acupoint GB17 backward along the meridian, international scalp acupuncture lines code MS9) corresponding to the user when the angle of the mounting portion 31 is adjusted, It should be noted that the positions adjusted by the aforementioned acupoint agents 61 can be adjusted in one position or at the same time, and it is not limited to this.

Referring to FIGS. 2, 5 and 7, the electronic stimulation unit 7 includes several electrical stimulation agents 71, which are electrically connected to the ends of the corresponding elastic conductive members 319 opposite to the conductive strips 312. Two of the electrical stimulation agents 71 are respectively arranged on the electrode mounting bases 318 of the mounting portion 31 in an adjustable position, and can move along the mounting slot 32 with the electrode mounting bases 318 to adjust their positions. Two of the electrical stimulation agents 71 are arranged on the front side portion 24, and the electrical stimulation agents 71 are used to output physical stimulation to the user's head. The electrical stimulation agents 71 located on the mounting portion 31 can be adjusted to the C3 position and C4 position respectively corresponding to the international 10-20 electroencephalogram electrode positions when the mounting portion 31 is adjusted in angle. In this embodiment, the physical stimulation is the direct current of transcranial direct current stimulation (TDCS), with a voltage of 1-12 V and a current of 0.5 mA and 5 mA, but it is not limited to this. It can also be an electromagnetic pulse for transcranial magnetic stimulation (TMS). The electromagnetic frequency is between 1 to 20 Hz, and the stimulation intensity is 90% aMT (active motor threshold) and 120% rMT (rest motor threshold). aMT and rMT are the definitions of the regular intensity of the TMS instrument, so this specification will not further explain.

Each electrical stimulation agents 71 has several conductive pillars 711 arranged in parallel to output physical stimulation. In this embodiment, each conductive pillar 711 is made of silicone electrode material.

The control unit 8 is electrically connected to the speakers 41, the optical frequency-flashed stimulation unit 5, the acupoint agents 61, the resistance measurement medium 62 and the electrical stimulation agents 71, and stores the digital information of the binaural beats with frequency following response, and can simultaneously control the speakers 41 to broadcast the binaural beats with frequency following response, the optical frequency-flashed stimulation unit 5 to display a flickering light, the acupoint agents 61 to emit physical stimulation and the electrical stimulation agents 71 to emit according to a preset command. In this embodiment, the digital information, the virtual image displayed by the optical frequency-flashed stimulation unit 5 and the preset command are downloaded through a cloud network 9 and then pre-stored in the control unit 8.

Figure 12:
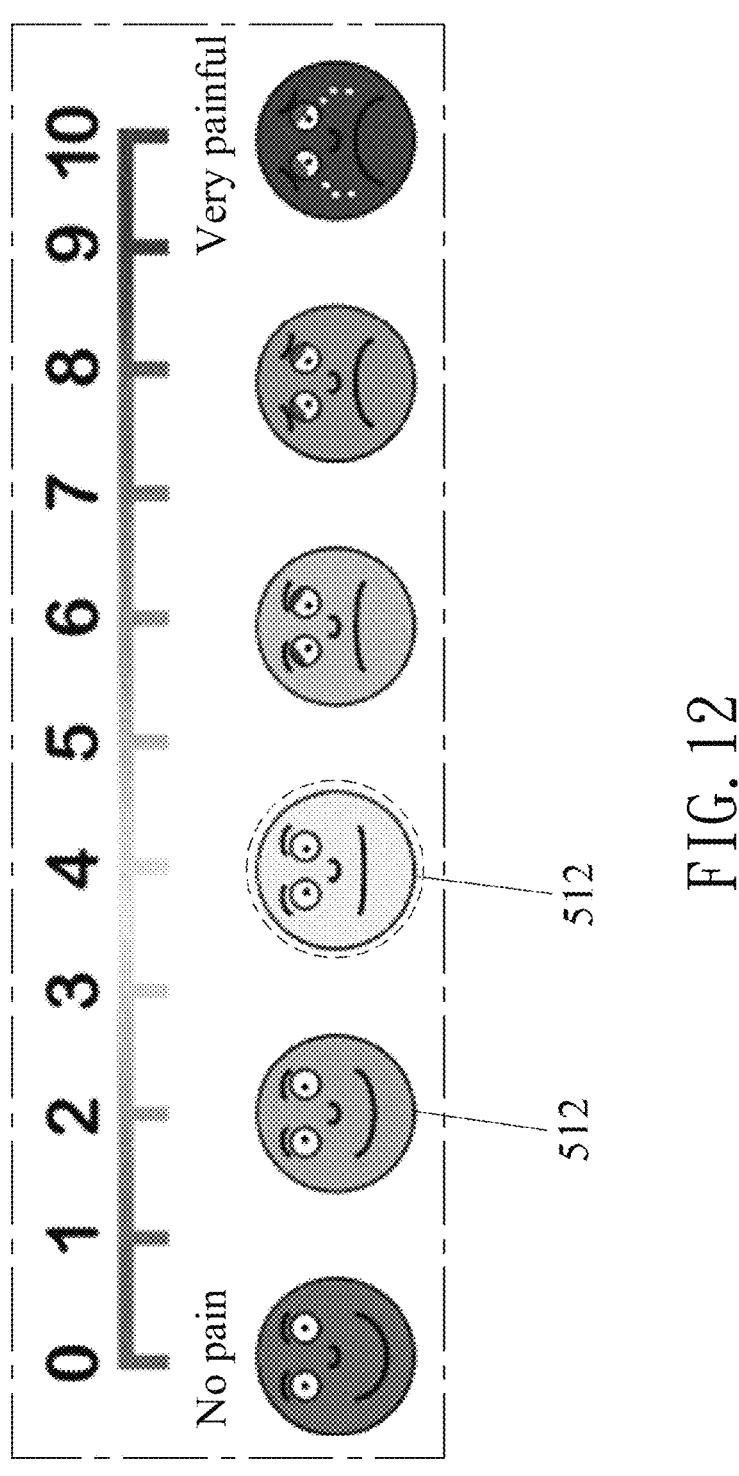
FIG. 12 is a display diagram of the embodiment when an assessment program is executed.

Referring to FIGS. 1, 2 and 12, the control unit 8 can execute an assessment program. In the assessment program, the control unit controls the display module 51 to display several pain self-assessment sheets 512 representing different pain degrees, and can change the selected pain self-assessment sheets 512 by changing the direction of the display module 51, and generate a pain self-assessment result corresponding to the selected pain self-assessment sheet 512 after confirmation by the operation button 52 for storage.

Referring to FIGS. 2, 6 and 7, when in use, the user first wears the wearable brain multi-stimulation pain control device, and measures the resistance through the resistance measuring medium 62 to position the acupoint agents 61. When the user's head contacts the electrical stimulation agents 71 arranged on the mounting portion 31, it will push against the elastic conductive members 319 to compress (see FIG. 10), so that make the conductive pillar 711 of the electrical stimulation agents 71 fit the top of the user's head. Then, the control unit 8 controls the speakers 41 to broadcast the binaural beats with frequency following response, causes the display module 51 of the optical frequency-flashed stimulation unit 5 to display a flickering light, causes the acupoint agents 61 to give physical stimulation to the corresponding acupuncture points, and causes the electro-stimulation medium 71 to give physical stimulation to the corresponding brain regions, so that the user can receive multi stimulation at the same time by the binaural beats with frequency following response, the flickering light, acupoint and brain regions, thereby achieving the effect of improving pain. In this embodiment, when the audio frequency difference is 20 Hz, the binaural beats with frequency following response gradually decreases by 1 HZ every minute until the audio frequency difference is maintained at 1 Hz.

In addition, the user can perform the assessment program before use to obtain the pain self-assessment result before operation, and then perform the pain self-assessment result again after the whole operation process. Through the two self-assessment results, the improvement degree of pain can be seen, which can be used as a record and as a driving force for the user to further use.

It is added that in this case, the physical stimulation of the isoelectric stimulation medium 71 can improve the pain, and the test results of improving the pain have been proved by the following references, so it will not be further explained in this specification.

1. Khedr E M, Omran E A H, Ismail N M, et al. Effects of transcranial direct current stimulation on pain, mood and serum endorphin level in the treatment of fibromyalgia: A double blinded, randomized clinical trial. Brain Stimul. 2017; 10(5):893-901. doi: 10.1016/j.brs.2017.06.006
2. Chang W J, Bennell K L, Hodges P W, Hinman R S, Young C L, Buscemi V, et al. Addition of transcranial direct current stimulation to quadriceps strengthening exercise in knee osteoarthritis: a pilot randomised controlled trial. PLOS ONE 2017; Vol. 12, issue 6: e0180328.
3. Hazime F A, Baptista A F, de Freitas D G, Monteiro R L, Maretto R L, Hasue R H. Treating low back pain with combined cerebral and peripheral electrical stimulation: a randomized, double-blind, factorial clinical trial. European Journal of Pain 2017; Vol. 21, issue 7:1132-43.

In addition, this case further carry out experiments. Five patients with chronic pain were treated with this binaural beats with frequency following response in both ears for 30 minutes, and the frequency difference was gradually reduced from 20 Hz to 1 Hz. After the treatment, the VAS (Pain Visual Scale) was measured, and it decreased by 10% on average compared with before the treatment, which proved that the binaural beats with frequency following response had the effect of improving pain.

In addition, five patients with chronic pain were treated with green flash treatment in both eyes for 30 minutes. The frequency varied from 20 Hz to 1 Hz, and the wavelength of green light was 495-570 nm. After the treatment, the VAS (Pain Visual Scale) was measured, and the average decrease was 11% compared with that before the treatment, which also proved that the optical frequency-flashed stimulation had the effect of improving pain.

This case was further verified by experiments. Five patients with chronic pain were treated with laser acupoint at their head points. The laser wavelength was 810 nm, the power was 150 mW, and the laser light was irradiated for 10 minutes. The irradiation sites are the midline of the head acupoints, the anterior oblique line of the apex and the posterior oblique line of the apex and the temporal point. After the treatment, the VAS (Visual Pain Scale) was measured, and the average decrease was 59% compared with that before the treatment, which proved that the laser treatment of relevant acupoints could improve the pain.

It is worth mentioning that in this case, the binaural beats with frequency following response, the flickering light, the acupoint agents 61 and the electrical stimulation agents 71 are used to stimulate at the same time, but they can also be stimulated separately, and are not limited to this.

To sum up, by arranging the speakers 41, the optical frequency-flashed stimulation unit 5, the acupoint agents 61 and the electrical stimulation agents 71, the user can obtain multiple stimuli at the same time in a single course of treatment, thus achieving the effect of relieving pain. Therefore, the purpose of the present invention can indeed be achieved.

However, the above are only examples of the present invention. While the scope of the present invention cannot be limited by this, all simple and equivalent changes and modifications made according to the patent application scope and the contents of the patent specification of the present invention are still within the scope of the present invention.

What is claimed is:

1. A wearable brain multi-stimulation pain control device for a user, the wearable brain multi-stimulation pain control device comprising:

a main support unit, which is adapted to correspond to the user's head shape, and includes two ear portions that are adapted to correspond to both ears of the user, a back side portion adjacent to the ear portions and adapted to span a back of the user's skull, and a front side portion adjacent to the ear portions and adapted to span a front of the user's skull;

a reference axis being defined as passing through the main support unit and adjacent to the ears portion, and an auxiliary support unit that includes a mounting portion adapted to correspond to the user's head shape, wherein two opposite ends of the mounting portion are pivotable on the main support unit around the reference axis, and the angle is adjustable along the outer side of the user's head;

an audio stimulation unit that comprises two speakers respectively arranged at the ear portions, which are configured to broadcast a binaural beats with frequency following response to both ears of the user, and the binaural beats has an audio frequency difference;

an optical frequency-flashed stimulation unit, which is arranged at the front side portion and is configured to stimulate at least one eye of the user with flickering light; and a control unit, electrically connected with the speakers and the optical frequency-flashed stimulation unit, stores digital information of the binaural beats with frequency following response, and is configured to simultaneously control the speakers to broadcast the binaural beats with frequency following response according to a preset command, and the optical frequency-flashed stimulation unit displays a flickering light;

wherein the flickering light displayed by the optical frequency-flashed stimulation unit is configured to stimulate the user's two eyes, with a predetermined frequency between 1 Hz to 20 Hz and with a generated light which is a green light with a wavelength between 495 nm and 570 nm, and the flickering light displayed by the optical frequency-flashed stimulation unit is configured to stimulate the user's two eyes with an optical frequency difference from 1 Hz to 20 Hz and with a generated light which is green light with a wavelength ranging from 495 nm to 570 nm.

2. The wearable brain multi-stimulation pain control device according to claim 1, further comprising an acupoint stimulation unit, the acupoint stimulation unit comprises a plurality of acupoint agents that are electrically connected to the control unit and respectively disposed on the mounting portion in an adjustable position, the acupoint agents are configured to output physical stimulation to user's head acupoints, and the position of the acupoint agents are adapted to correspond user's acupoint GV20 and a position between an anterior oblique line of vertex-temporal and a posterior oblique line of vertex-temporal of the user.

3. The wearable brain multi-stimulation pain control device according to claim 2, wherein the acupoint agents is configured to emit laser light, and a laser light wavelength of the acupoint agents is between 500 nm and 1300 nm, and an output power is between 5 mW~500 mW.

4. The wearable brain multi-stimulation pain control device according to claim 2, wherein at least one of the acupoint agents is adapted to be adjusted to a position that is adapted to correspond to the user's the middle line of vertex when the auxiliary support unit adjusts the angle.

5. The wearable brain multi-stimulation pain control device according to claim 2, wherein one of the acupoint agents is adapted to be adjusted to a position that is adapted to correspond to the user's anterior oblique line of vertex-temporal when the angle of the mounting portion is adjusted.

6. The wearable brain multi-stimulation pain control device according to claim 2, wherein one of the acupoint agents is adapted to be adjusted to a position that is adapted to correspond to the user's posterior oblique line of vertex-temporal when the angle of the mounting portion is adjusted.

7. The wearable brain multi-stimulation pain control device according to claim 2, wherein one of the acupoint agents is adapted to be adjusted to a position that is adapted to correspond to the user's the lateral line 1 of vertex when the angle of the mounting portion is adjusted.

8. The wearable brain multi-stimulation pain control device according to claim 2, wherein one of the acupoint agents is adapted to be adjusted to a position that is adapted to correspond to the user's the lateral line 2 of vertex when the angle of the mounting portion is adjusted.

9. The wearable brain multi-stimulation pain control device according to claim 2, wherein the acupoint stimulation unit further includes at least one resistance measurement medium electrically connected to the control unit and adjacent to the acupoint agents, each of which is configured to measure a body resistance of the user to confirm whether the corresponding acupoint agents is located in a low-resistance acupoint area.

10. The wearable brain multi-stimulation pain control device the according to claim 2, wherein the auxiliary support unit further comprises at least one mounting slot located at the mounting portion and extending between the ear portions, the acupoint agents are configured to move along the mounting slot to adjust the position, wherein the mounting portion has a rail member adapted to correspond to the user's head shape, and a plurality of conductive strips arranged at intervals on the side of the rail member are adapted to correspond to the user and the conductive strips extend between the ear portions, a plurality of sliding members arranged on one side of the conductive strips are adapted to correspond to the user and configured to move along the rail member to adjust the position, a plurality of screw locking members that pass through the corresponding mounting slots from one side of the rail member, which are opposite to the sliding members, and are respectively screwed to the sliding members for fixing the sliding members, a plurality of positioning members respectively slidably passed through the screw locking members from one side of the screw locking members, which are opposite to the sliding members, a plurality of laser mounting bases that are arranged on one side of the sliding members, which are opposite to the rail member, and respectively screwed to the positioning members, a plurality of conductive members, the number of connecting conductive members corresponding to each laser mounting base is the same as that of the conductive strips, the connecting conductive members corresponding to each laser mounting base pass through the corresponding sliding member and the laser mounting base, and one end is electrically connected to the corresponding acupoint agents, and the other end is electrically connected to the corresponding conductive strip.

11. The wearable brain multi-stimulation pain control device according to claim 1, wherein the optical frequency-flashed stimulation unit is a virtual image wearable device, and includes a display module and an operation button, the control unit is configured to execute an assessment program, in the assessment program, the control unit controls the display module to display a plurality of pain self-assessment lists representing different pain degrees, and is configured to change the selected pain self-assessment sheets by changing the direction of the display module, and generate a pain self-assessment result corresponding to the selected pain self-assessment sheet after confirmation by the operation button for storage.

12. The wearable brain multi-stimulation pain control device according to claim 1, wherein an audio frequency difference of the binaural beats with frequency following response is between 1 Hz to 20 Hz.

13. The wearable brain multi-stimulation pain control device according to claim 12, wherein the beat binaural beats with frequency following response is composed of an audio frequency difference of 20 Hz, and gradually decreases by 1 Hz every minute until the audio frequency difference is maintained at 1 Hz.

14. The wearable brain multi-stimulation pain control device according to claim 1, further comprising an electronic stimulation unit, the electronic stimulation unit comprising a plurality of electrical stimulation agents, which are electrically connected to the control unit, two of the electrical stimulation agents are respectively arranged on the mounting portion in an adjustable position, and are configured to move along the mounting slot to adjust their positions, one of the electrical stimulation agents are arranged on the front side portion, the electrical stimulation agents are configured to output physical stimulation to the user's head, the electrical stimulation agents located on the mounting portion are configured to be adjusted to the C3 position and C4 position respectively corresponding to the international 10-20 electroencephalogram electrode positions when the mounting portion is adjusted in angle.

15. The wearable brain multi-stimulation pain control device according to claim 14, wherein when the electrical stimulation agents are configured to output direct current, the voltage is between 1 and 12V, and the current is between 0.5 mA and 5 mA, when these electrical stimulation agents are configured to output electromagnetic pulses, the electromagnetic frequency is between 1-20 Hz.

16. The wearable brain multi-stimulation pain control device according to claim 14, wherein each electrical stimulation agent has a plurality of conductive pillars arranged in parallel to output physical stimulation, and each conductive pillar is made of a-silicone.

17. The wearable brain multi-stimulation pain control device as claimed in claim 14, wherein the auxiliary support unit further comprises at least one mounting slot located at the mounting portion and extending between the ear portions, wherein the electrical stimulation agents located in the mounting portion are configured to move along the mounting slot to adjust the position, wherein the mounting portion has a rail member adapted to correspond to the head shape of the user, and a plurality of conductive strips arranged at intervals on the side of the rail member are adapted to correspond to the user and the conductive strips extend between the ear portions, a plurality of sliding members arranged on one side of the conductive strips are adapted to correspond to the user and are configured to move along the rail member to adjust the position, a plurality of screw locking members that pass through the corresponding mounting slots from one side of the rail member, which are opposite to the sliding members, and are respectively screwed to the sliding members for fixing the sliding members, a plurality of positioning members respectively slidably passed through the screw locking members from one side of the screw locking members, which are opposite to the sliding members, a plurality of electrode mounting base that are arranged on one side of the sliding members, which are opposite to the rail member, and respectively screwed to the positioning members, a plurality of compressible elastic conductive member, the number of elastic conductive member, corresponding to each electrode mounting base is the same as that of the conductive strips, the connecting elastic conductive member corresponding to each electrode mounting base pass through the corresponding sliding member and the electrode mounting base, and one end is electrically connected to the corresponding electrical stimulation agents, and the other end is electrically connected to the corresponding conductive strip.

18. The wearable brain multi-stimulation pain control device according to claim 1, wherein the main support unit further comprises a top side portion.

19. The wearable brain multi-stimulation pain control device according to claim 1, wherein the digital information and the preset command are configured to be downloaded through a cloud network and pre-stored in the control unit.

* * * * *